United States Patent [19]

Shepard

[11] Patent Number: 4,994,080
[45] Date of Patent: Feb. 19, 1991

[54] OPTICAL LENS HAVING AT LEAST ONE STENOPAEIC OPENING LOCATED IN THE CENTRAL AREA THEREOF

[76] Inventor: Dennis D. Shepard, 1414 E. Main St., Santa Maria, Calif. 93454

[21] Appl. No.: 220,012

[22] Filed: Jul. 15, 1988

[51] Int. Cl.$^5$ .................... A61F 2/14; A61F 2/16; G02C 7/04
[52] U.S. Cl. ............................ 623/5; 623/6; 351/160 R; 351/161; 351/162
[58] Field of Search ............. 623/5, 6; 351/160, 161, 351/162, 168, 171

[56] References Cited

U.S. PATENT DOCUMENTS

| | | | |
|---|---|---|---|
| 3,507,566 | 4/1970 | Knapp | 351/160 R |
| 3,688,386 | 9/1972 | Pereira | 351/160 X |
| 4,666,267 | 5/1987 | Wichterle | 351/162 X |

FOREIGN PATENT DOCUMENTS

WO86/03961  7/1986  PCT Int'l Appl. .............. 623/6

Primary Examiner—Ronald Frinks
Attorney, Agent, or Firm—Daniel J. Meaney, Jr.

[57] ABSTRACT

An optical lens having a transparent lens body for a human eye or mammalian eye is shown. The transparent lens body has an anterior surface and a posterior surface and has formed in the central area thereof at least one stenopaeic opening which is substantially perpendicular to the anterior surface and posterior surface of the lens body. The at least one stenopaeic opening has a dimension "d" which is selected to be a geometrical dimension such that an image of an object located in front of the lens, when the lens is implanted in, or placed upon, the eye, is projected through the lens generally along a predetermined light transmitting path defining the visual axis of an eye and onto the fovea centralis of the eye which is located in back of the lens. The optical lens containing the at least one stenopaeic opening selectively intercepts and passes light through the lens body along the visual axis onto the fovea centralis in a manner to obtain an optical effect by increasing the depth of focus of the eye in order to substitute for the loss of at least one of the focusing power and the accommodation of the eye. Also disclosed herein is an optical lens having at least one stenopaeic opening located substantially central or paracentral therein and having a plurality of stenopaeic openings spaced from and positioned around the at least one stenopaeic opening wherein each one of the plurality of stenopaeic openings has a selected dimension "d".

21 Claims, 2 Drawing Sheets

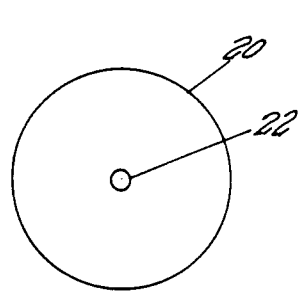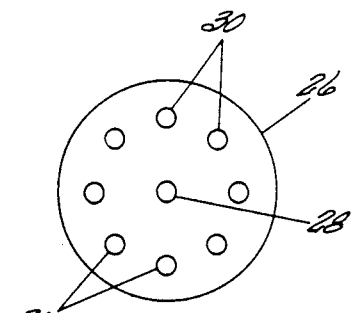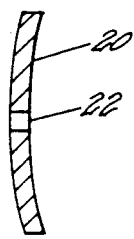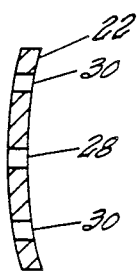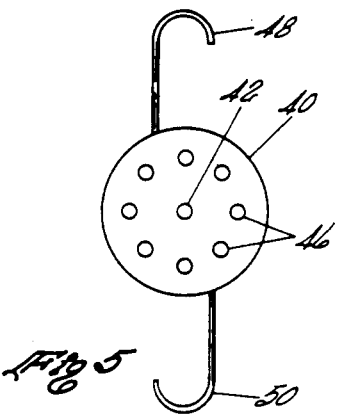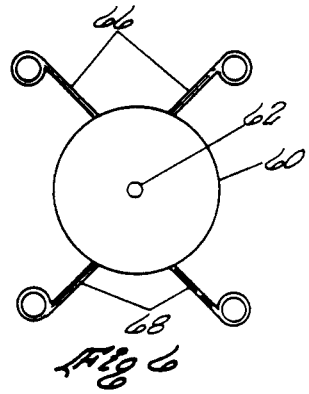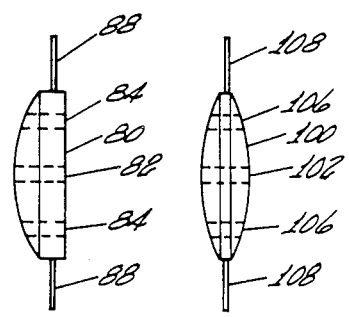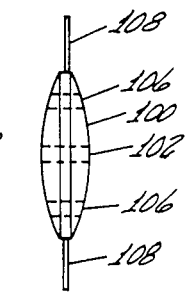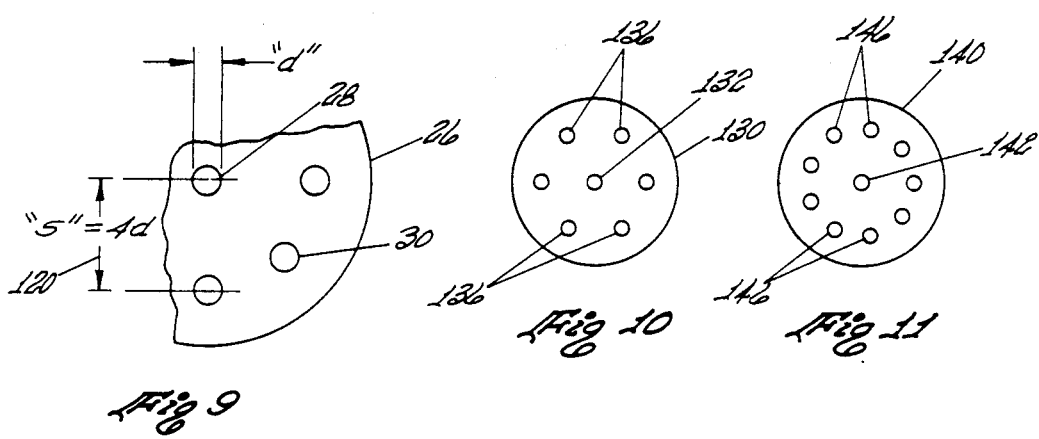

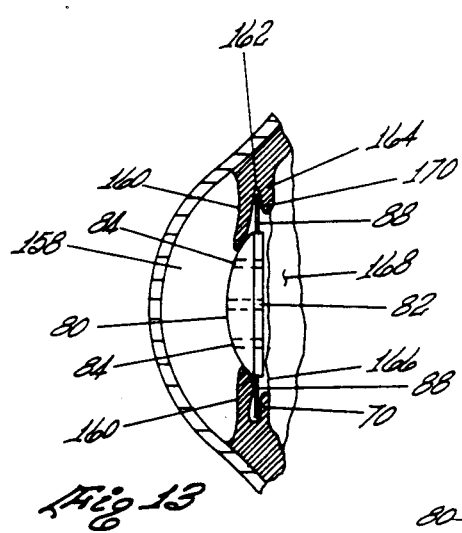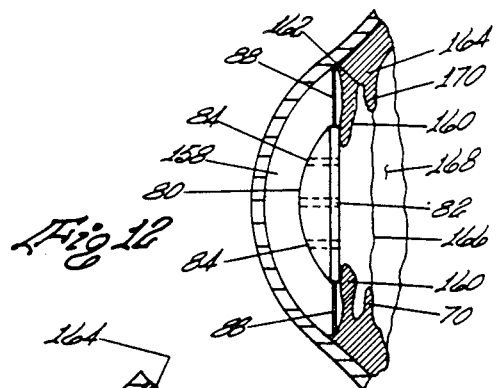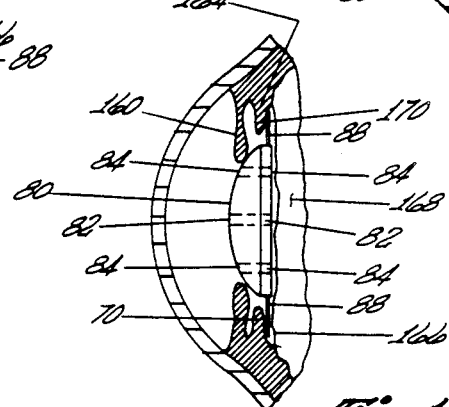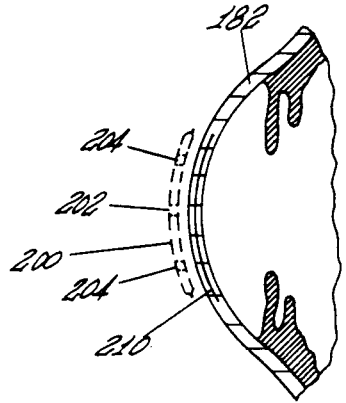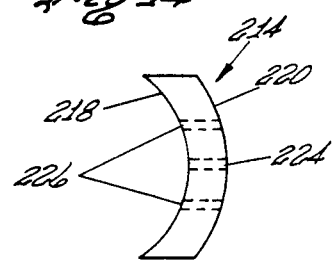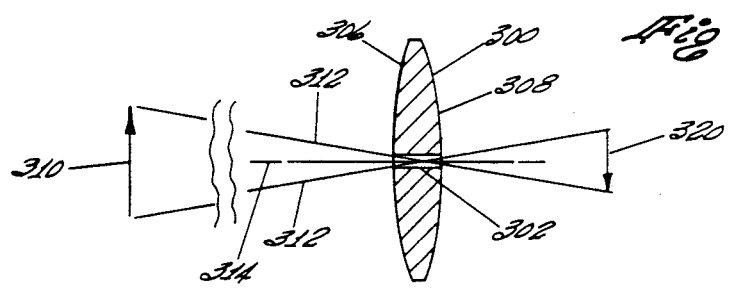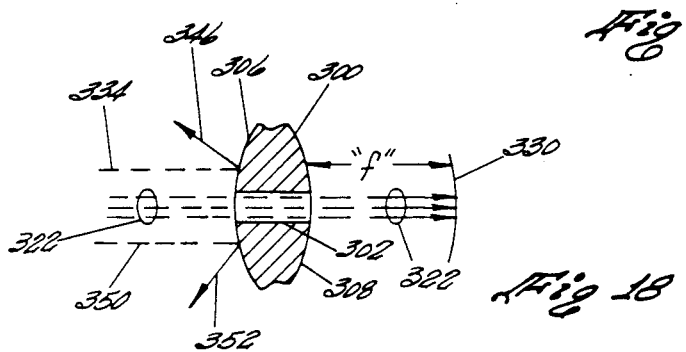

OPTICAL LENS HAVING AT LEAST ONE STENOPAEIC OPENING LOCATED IN THE CENTRAL AREA THEREOF

BACKGROUND OF THE INVENTION

1. Field of the Invention

This invention relates to an optical lens for a human eye or mammalian eye (hereinafter included in the term "eye" as used herein), which comprises a transparent lens body which is adapted to be placed onto, into or implanted within the eye to obtain an optical effect by increasing the normal depth of focus of the eye in order to substitute for the loss of at least one of the focusing power and the accommodation of the eye and, more particularly, relates to an optical lens having a transparent lens body wherein the transparent lens body has formed in the central area thereof at least one stenopaeic opening to selectively intercept and pass light through the lens body along the visual axis of the eye onto the fovea centralis of the eye to obtain the desired optical effect by increasing the normal depth of focus of the eye in order to substitute for the loss of at least one of the focusing power and the accommodation of the eye.

2. Description of the Prior Art

It is well known in the art to utilize an intraocular lens, a corneal overlay, contact lens or other special lens which can be implanted into the eye to obtain an optical effect for the eye as a substitution of the loss of both the focusing power or the accommodation of the eye.

It is well known to persons skilled in the art to test the visual acuity of a patient by using a multiple pinhole testing device. The multiple pinhole testing device which is used for testing the eye is in the form of a dark or nontransparent member having a "pinhole" formed in the center thereof and a plurality of "pinholes" spaced radially about the center "pinhole." One typical multiple pinhole testing device has a single center "pinhole," a first ring comprising eight multiple "pinholes" arranged equi-distantly and equi-angular around the center "pinhole" and a second ring of eight multiple "pinholes" formed with a larger radius and spaced at equal distance from and positioned at equal angles around the central stenopaeic opening. By use of the multiple pinhole testing device, an ophthalmologist can quickly test a patient to see if the patient's vision can be corrected by use of a lens compared to the visual loss due to the eye being diseased. An example of using such a multiple pinhole testing device is as follows: Assume that a hypothetical patient has a vision of 20/60. The patient looks through a hole of the multiple pinhole testing device. If the eye can be optically corrected, the patient would obtain or experience 20/20 vision by viewing an object through any one of the pinholes in the multiple pinhole testing device. However, if the patient's vision is not improved, that is, still remains 20/60 when viewing through the pinhole, then the ophthalmologist may conclude that the eye has a disease affecting the vision.

It is also well known in the art to utilize what is referred to as a "pinhole camera," that is, a camera which has no lens. Typically, such a camera consists of a darkened box with a small hole on one side, so that an image of an outside object is projected on the opposite side inside the box where it is recorded on photographic film.

It is also known in the art to have intraocular lenses which have positioning holes formed therethrough. Typical of such intraocular lens is a lens offered for sale and sold by Iolab Corporation referred to as the Model 103J Posterior Chamber Lens. One example of such a lens, is a lens having a 13 mm. haptic diameter, 6 mm. optic diameter, two positioning holes 180° apart and located parallel to the plano surface. In the Iolab Corporation Model 103J Posterior Chamber Lens, the positioning holes are located on the edge of or peripherally on the lens body and are utilized by an ophthalmologist for positioning the lens within the eye, and not for the purpose of providing an optical effect.

It is also known in the art that contact lens have very small, porous openings to pass metabolic gases such as oxygen or carbon dioxide to prevent swelling or loss of clarity of the cornea.

It is also known in the art to utilize a contact lens which can be characterized as a multi-focal length contact lens. Typical of such lens are those disclosed in U.S. Pat. No. 3,270,099 and 3,034,403. U.S. Pat. No. 3,270,099 discloses a lens which has a central portion of one optical power formed of one material and a peripheral portion of a different optical power surrounding the central portion. The central and peripheral portions are arranged so that their optical axes coincide and the central portion has a select dimension. U.S. Pat. No. 3,270,099 discloses that the central portion is either formed to be on the surface of the lens body or implanted within the lens body to obtain the desired optical effect.

U.S. Pat. No. 3,034,403 discloses a lens which may be formed of a black or dark absorption area occupying the entire thickness of the central area of the lens and having a small plug of a clear or lighter area to fabricate a "pinhole" type of contact lens. In the structure of a contact lens formed of U.S. Pat. No. 3,034,403, the lens body which is formed of two different materials, the center of which is transparent and the outer peripheral area of which is dark or black.

U.S. Pat. No. 4,010,496 discloses a bifocal lens which is adapted to be implanted into the anterior chamber of the eye having an air space in the upper lens edge to position the lens at the upper edge of the pupil in a dilated and constricted state. The air space is utilized for positioning on the lens, and is not intended to nor does it provide any optical effect.

U.S. Pat. No. 4,485,499 discloses an intraocular posterior chamber lens having two spaced elongated ridges which are located on the back surface of the lens so as to contact the posterior capsule and to keep the posterior capsule away from the back side of the lens. In the event of haziness or opacification of the posterior capsule, the open zona formed by the ridges between the rear of the lens and the posterior capsule allows corrective or restorative openings to be made in the posterior capsule. The so provided ridges do not have any optical correction effect.

A recent study disclosed in an article encaptioned HOLES IN CLEAR LENS DEMONSTRATE A PINHOLE EFFECT by Peter Zacharia, David Miller, M.D. appeared in the Apr., 1988, issue of ARCHIVES of OPHTHALMOLOGY, Volume 106, Pages 511-513, (referred to herein as the "Zacharia-Miller Reference") describes a new variant of the pinhole testing principle utilizing holes drilled in clear plastic lenses. A study discloses that holes drilled in a clear plastic lens held in combination with a blurring lens can overcome the blurring effect as much as a traditional pinhole. Specifically, the study disclosed that holes of a different diameter placed in lenses of different spherical power can improve visual acuity that had been degraded by a series of blurred spherical lenses. The study concluded that, in general, a hole in a clear lens improves visual acuity for progressively stronger blurring lenses. The study disclosed that the material utilized for the lens was a clear plastic lens, and the clear plastic lens was positioned by the lens relative to a patient s eye so that the patient can view the target, which in this case was Snellen-type E target at 75-foot-candle illumination, through the small hole drilled in the plastic lens. In front of the plastic lens having the hole there was placed a spherical convex blurring lens that degraded the image. The visual acuity improvement (VAI) was defined as follows: VAI=(visual acuity through pinhole and clear lens and blurring lens)×0.1/visual acuity through blurring lens alone. This study did not suggest, disclose or teach using a transparent lens body having a "pinhole" formed therethrough as a means for selectively intercepting and passing light through a lens body onto the retina or the fovea centralis in a manner to obtain an optical effect by increasing the normal depth of focus of the eye in order to substitute for the loss of at least one of the focusing power and the accommodation of the eye.

SUMMARY OF THE PRESENT INVENTION

This invention discloses a novel and unique artificial lens or optical lens for an eye which utilizes at least one stenopaeic opening as a means for obtaining an optical effect by increasing the normal depth of focus of the eye in order to suhstitute for the loss of at least one of the focusing power and the accommodation of the eye. The optical lens disclosed herein includes a transparent lena body having an anterior surface and a posterior surface. The lens body has formed in the central area thereof at least one stenopaeic opening which is substantially perpendicular to the anterior surface and posterior surface. The stenopaeic opening has a dimension "d" which is selected to be that geometrical dimension that would be required such that an image of an outside object located on one side of the lens, when implanted in the eye, is projected through the lens generally along a predetermined light transmitting path defining the visual axis of the eye, onto the fovea centralis of the eye located on the opposite side of the lens. The at least one stenopaeic opening selectively intercepts and passes light through the lens body along the visual axis onto the fovea centralis in a manner to obtain an optical effect by increasing the normal depth of focus of the eye in order to substitute for the loss of at least one of the focusing power and the accommodation of the eye.

In the preferred embodiment, the at least one stenopaeic opening is an opening which is circular in shape having a selected diameter which corresponds to the dimension "d."

In another embodiment of the invention, a plurality of stenopaeic openings can be formed in the lans body wherein the plurality of stenopaeic openings are spaced from and positioned around the at least one stenopaeic opening to form multiple pinholes around the at least on stenopaeic opening which is adapted to accommodate a range of dimensional variances which occur between different eyes.

The use of a multiple-pinhole testing device and the Zacharia-Miller Reference discloses that it is known in the art to utilize an external sheet of material having a hole formed therethrough for testing purposes. However, heretofore, there has been no disclosure, suggestion or teaching to utilize a transparent lens body having a stenopaeic opening formed therethrough to selectively intercept and transmit light beams which are entered upon the center of the lens wherein the stenopaeic opening functions as a focusing means to transmit the rays representing the image along the visual axis of the eye and onto the fovea centralis.

U.S. Pat. No. 3,034,403 discloses a contact lens having apparent variable light absorption characteristics. Specifically, U.S. Pat. No. 3,034,403 discloses either utilizing a lens made of clear plastic material which has a hole drilled therethrough wherein a colored plug or rod is inserted into the hole and the plug or rod is then cemented into position for further processing. In the alternative, the process for forming the lens discloses using the pupil or pinhole type contact lens by starting with a black or dark colored blank and inserting a small plug of clear plastic therein. U.S Pat. No. 3,034,403 further discloses that either of the methods may also be used for implanting the lens. The specific embodiment descrlbed above is shown in FIG. 5 of that Patent.

U.S. Pat. No. 3,034,403 did not disclose, suggest or teach utilizing a transparent lens body as part of an optical lens and for providing in the lens body in the central area thereof at least one stenopaelc opening which is substantially perpendicular to the top and posterior surface and which is utilized to selectively intercept and pass light through the lens body along a visual access onto the fovea centralis in a manner to obtain an optical effect by increasing the normal depth of focus of the eye in order to substitute for the loss of at least one of the focusing power and the accommodation of the eye.

U.S. Pat, No. 3,270,079 discloses a contact lens having a multiple focal length, but the lens is formed completely of different types of material and the optical effect of each of the different types of materials are utilized for making the contact lens a multi-focal length contact lens. Again, there is not a suggestion, disclosure or teaching that a stenopaeic opening be formed in the central body thereof for the purpose described hereinbefore.

U.S. Pat. No. 4,485,499 discloses ridges, or elongated rails, which perform a function other than correcting visual acuity in a lens.

ln U.S. Pat. No. 4,010,496, the air space located in the upper lens edge is used to mechanically position the lens at the upper edge of the pupil. This patent does not suggest, disclose or teach the invention as described hereinbefore.

The Iolab Corporation Model 103J Posterior Chamber Lens discloses positioning holes which are used for mechanically positioning the lens in the eye and not for correction of optical effect as disclosed herein. Thus, there is no disclosure, suggestion, or teaching that positioning holes be utilized as an stenopaeic opening.

It is known in the art that small holes can be drilled through a hard plastic contact lens to increase oxygen or carbon dioxide transmission, and it is known that these holes are not for optical accommodation or dioptic power purposes.

The optical lens of the present invention results in a unique, novel and improved device which can be utilized to enhance or improve the manner in which an intraocular lens or artificial lens is utilized to obtain an optical effect by increasing the normal depth of focus of the eye in order to substitute for the loss of at least one of the focusing power and the accommodation of the eye.

One advantage of the present invention is that the optical lens can be formed having a transparent lens body and a hole can be drilled into the central area thereof having a dimension "d," that dimension "d" being a selected dimension as described herein. The at least one stenopaeic opening selectively passes light rays which are essentially parallel with the central axis oi the at least one stenopaeic opening and for transmitting the same along a predetermined light transmitting path defining a visual axis of the eye and onto the fovea centralis thereof generallY located in the area of the retina.

Another advantage of the present invention is that an optical lens or artificial lens having a transparent lens body having the at least one stenopaeic opening can result in the lens having an improved optical effect by increasing the normal depth of focus of the eye in order to substitute for the loss of at least one of the focusing power and the accommodation of the eye.

Another advantage of the present invention is that the at least one stenopaeic opening is located substantially along the central axis of the lens. As will be described hereinbelow, it is not necessary that the at least one stenopaeic opening be located generally on the central axis on the lens in that the optical center of an eye varies from eye to eye and the brain compensates for such differences.

Another advantage of the present invention is that the size of the at least one stenopaeic opening can have a dimension which is selected to be in the range of about 0.5 mm to about 3.00 mm.

Another advantage of the present invention is that the optical lens body can have any of the well known shapes, such as for example, a plano disc lens, a plano-convex lens, a biconvex lens, concavo-convex lens, or a lens with specific dioptic power.

Another advantage of the present invention is that the optical lens having a transparent body containing the at least one stenopaeic opening can be utilized with resilient means or haptics and is adapted to be implanted into the anterior chamber or the posterior chamber of the eye.

Another advantage of the present invention is that the lens body forming the optical lens can be a contact lens, can be a corneal overlay or could be an artificial lens which is adapted to be implanted into the corneal stroma.

BRIEF DESCRIPTION OF THE DRAWING

The foregoing and other advantages of this invention will be apparent from the following description of the preferred embodiment of the invention when considered with the illustrations and accompanying drawings which include the following figures:

FIG. 1 is a pictorially representation of an optical lens for an eye having a transparent lens body having formed in the central area thereof at least one stenopaeic opening;

FIG. 2 is a representation of an optical lens having a transparent body lens having at least one stenopaeic opening located in the center thereof and a plurality of atenopaeic openings spaced from and positioned around the at least one stenopaeic opening;

FIG. 3 is a cross-sectional view of the optical lens of FIG. 1;

FIG. 4 is a cross-sectional view of the optical lens of FIG. 2;

FIG. 5 is a pictorial representation of an optical lens having a transparent body, at least one stenopaeic opening, a plurality of stenopaeic openings formed thereon, the at least one stenopaeic opening and having two resilient means or haptics extending therefrom;

FIG. 6 is another embodiment of an intraocular lens having a transparent lens body having at least one stenopaeic opening and having four resilient support means for centering the optical lens in the human eye or mammelian eye;

FIG. 7 is an illustration of a plano-convex lens having at least one stenopaeic opening located in the central area thereof and a plurality of stenopaeic openings formed therearound;

FIG. 8 is a biconvex intraocular lens wherein the lens body has at least one stenopaeic opening and a plurality of stenopaeic openings formed therearound;

FIG. 9 is a partial pictorial illustration of the lens of FIG. 2 showing that the at least one stenopaeic opening has a dimension "d" and that the plurality of stenopaeic openings formed therearound are spaced radially a distance "s" from the at least one stenopaeic opening;

FIG. 10 is another embodiment of an optical lens having a transparent body having an at least one stenopaeic opening and six stenopaeic openings formed therearound;

FIG. 11 is another embodiment of an optical lens having a transparent body having an at least one stenopaeic opening and ten stenopaeic openings formed therearound;

FIG. 12 is a pictorial representation of a human eye having an optical lens of the present invention located in the anterior chamber of the eye;

FIG. 13 is a pictorial representation of a human eye having an optical lens of the present invention located in the posterior chamber of the eye but forward of the posterior capsule:

FIG. 14 is a pictorial representation of a human eye having an optical lens of the present invention located in the posterior chamber of the eye and adjacent the posterior capsule;

FIG. 15 is a pictorial representation of the human eye showing an optical lens having a transparent lens body using the teachings of the present invention implanted in the corneal stroma or utilized as a corneal overlay or as a contact lens;

FIG. 16 is a pictorial illustration of a concavo-convex lens having at least one stenopaeic opening located in the central area thereof and a plurality of stenopaeic openings formed therearound;

FIG. 17 is a pictorial representation of an optical lens having a transparent lens body showing the focusing effect produced by the at least one stenopaeic opening; and FIG. 18 is a pictorial representation of the optical lens selectively intercepting and transmitting light along a predetermined light transmitting path defining the visual axis of an eye and focusing the same on the fovea centralis.

DESCRIPTION OF THE PREFERRED EMB0DIMENT

FIG. 1 illustrates an optical lens for an eye comprising a transparent lens body 20 having an anterior surface and a posterior surface. The lens body 20 has formed in the central area thereof at least one stenopaeic opening 22 which is substantially perpendicular to the top and posterior surface. The dimension "d" of the at least one stenopaeic opening is selected to be a geometrical dimension such that an image of an outside object located on one side of an implanted lens is projected through the lens generally along a predetermined light transmitting path defining the visual axis of an eye. The light beams are focused onto the fovea centralis which is located on the opposite side of the lens. The lens body 20 functions to selectively intercept and pass light through the lens body 20 along the visual axis onto the fovea centralis in a manner to obtain an optical effect by increasing the normal depth of focus of the eye in order to substitute for the loss of at least one of the focusing power and the accommodation of the eye.

This is one significant improvement, because an optical lens fabricated using the teachings of this invention can provide the optical effect by increasing the depth of focus of the eye in order to substitute for either a loss of the focusing power or the loss of the accommodation of the eye, or both together.

FIG. 2 illustrates another embodiment of optical lens for an eye having a transparent lens body 26. In FIG. 2, the lens body 26 has at least one stenopaeic opening 28 which is generally located along the optical axis of the lens. A plurality of stenopaeic openings 30 are located radially around the at least one stenopaeic opening are spaced equi-angularly around the at least one stenopaeic opening 28.

When the optical lens is implanted into an eye, the lens collects light received and passed by the at least one stenopaeic opening and functions to focus the same on the fovea centralis located in the rear portion of the eye. When the lens has a plurality of stenopaeIc openings, each of the openings selectively intercept and pass the image to the eye. The eye, through the brain, focuses on the hole which is nearest the optical center of the eye.

Because of the cerebral phenomenon of the brain being able to focus then on an image nearest the fovea centralis, the embodiment of the optical lens having a transparent body having a plurality of stenopaeic openings will function appropriately to obtain the desired optical effect by increasing the normal depth of focus of the eye in order to substitute for the loss of at least one of the focusing power and the accommodation of the eye.

One other advantage of the embodiment of FIG. 2 is as follows: The anatomical center of the human eye is not necessarily the optical center of the human eye. The anatomical center of the human eye is calculated or derived from measurement of the diameter of the cornea, and this dimension can be obtained by using techniques well known in the art. However, the optical center of the human eye is generally slightly nasal and downward relative to the anatomical center.

The angular difference between the optical center and the anatomical center is generally known in the art as the angle kappa (k). For example, the optical center may be 3° nasal and 1.5° inferior to the anatomical center. It is known in the art that the above angular diiferences could be as much as about 6° to about 7° or more.

The optical lens of the embodiment illustrated in FIG. 2 can be used if a patient, into which the lens is to be implanted or mounted, has a large difference between the anatomical center and the optical center. In such an application, it is possible for the eye to focus on one of the peripheral stenopaeic openings for the image rather than the at least one stenopaeic opening located in the central area of the lens. Thus, when such a lens is implanted into or onto the eye of a patient and the patient has a large angle of difference (angle kappa) between the anatomical center and the optical center, the eye, through the cerebral phenomenon, will automatically focus on the nearest stenopaeic opening in order to receive the clearest or best focused image.

FIG. 4 illustrates that the center axis of the at least one stenopaeic opening 28 which is essentially parallel to the central axis of the plurality of stenopaeic openings 30 so that the light rays are passed through the lens along a substantially parallel path.

FIG. 5 illustrates an emhodiment generally referred to as the "Shearing" type intraocular lens. In FIG. 5, the optical lens includes a transparent lens body 40 having at least one stenopaeic opening 42 located along the central axis thereof and a plurality of spaced, equally angularly disposed stenopaeic openings 46 positioned therearound. The lens body 40 is supported by a pair of resilient support means, 48 and 50, sometimes referred to as haptics. The annular shaped ends of the resilient means 48 and 50 generally extend in the same direction and are utilized to provide centering of the lens implanted into the anterior or posterior chamber of the eye.

FIG. 6 illustrates another embodiment of the present invention generally referred to as the "Shepard" type intraocular lens. The optical lens includes a lens body 60 having an at least one stenopaeic opening 62. The optical lens of FIG. 6 includes four (4) resilient support means which are generally grouped as upper support means 66 and lower support means 68 The annular shaped ends of the resilient means 66 to 68 are positioned to prevent rotation of the lens 60 within the eye while permitting the intraocular lens to be centered within the eye.

FIG. 7 illustrates another embodiment of the present invention wherein the optical lens is formed to have a plano surface and a convex surface sometimes referred to as a planoconvex lens. In the embodiment of FIG. 7, the lens body 80 has at least one stenopaeic opening 82 formed along the central axis thereof and a plurality of stenopaeic openings 84 located therearound. Resilient means 88 are utilized to center the optical lens within the appropriate chamber of a human eye or mammelian eye.

FIG. 8 illustrates another embodiment of a biconvex lens surface having a lens bodY 100 which has an at least one stenopaeic opening 102 formed in the central area thereof and a plurality of stenopaeic openings 106 formed therearound. Resilient support means 108 are utilized for positioning the optical lens in the appropriate chamber of an eye.

FIG. 9 illustrates in greater details the relationship between the positioning of the at least one stenopaeic opening 28 of FIG. 2 and its relationship to the plurality of stenopaeic openings 30 formed therearound. As illustrated in FIG. 9, the at least one stenopaeic opening 28 is shown to have a geometrical dimension "d." In the embodiment of FIG. 9, the at least one atenopaeic opening is circular shaped and the dimension is equal to the diameter of that opening. The plurality of stenopaeic openings 30 formed around the at least one stenopaeic opening 28 is spaced radially and equi-angularly around the lens periphery. The distance or radius of the plurality of holes is equal to "s." The distance "s" is defined to be equal to four times the dimension "d." Thus, the formula is as follows:

$$s = 4d.$$

The selection of the geometrical dimension "d" and the geometrical distance "s" is established by several important criteria. The light beams passing through the at least one stenopaeic opening 28 travels along the predetermined light transmitting path which defines the visual axis of the eye and the light beams are focused onto the fovea centralis. The fovea centralis is an area referred to as a macula upon which the image is actually focused.

If the dimension of the at least one stenopaeic opening 28, or any one of the plurality of the stenopaeic openings 30 formed therearound, is too large, the extraneous light is transmitted along the light path and onto the fovea centralis. As a result, the extraneous light is interpreted by the brain as aberrant light resulting in a confusing image. On the other hand, if the dimension of the stenopaeic opening is too small, not enough light is transmitted therethrough and the brain would be unable to interpret the appropriate image. Thus, in the situation where the stenopaeic opening is too small, the illumination available from the light rays would be too small to form a good visual image which can be interpreted by the brain.

There are other factors which affect the transparency of the lens. For example, the lens body can be tinted with a UV filter or other light absorbing materials which may be used to protect the eye providing an effect which is equivalent to that of the effect of "sunglasses" for the eye. Thus, the transparent lens could be a translucent lens having a UV filter formed thereon, but still have an stenopaeic opening "d" of the selected dimension which results in the appropriate image being focused onto the fovea centralis. Thus, the dimension "d" is selected to be that geometrical dimension for a human eye (or mammelian eye) such that an image of an outside object located on one side of the implanted lens is projected through the lens generally along a predetermined transmitting path along the visual axis of the eye and focused onto the fovea centralis of the eye located on the opposite side of the lens. The lens passes only those light beams which are substantially parallel to the central axis of the stenopaeic opening and rejects those light beams which ar transversing along a path other than such a parallel path or which are outside of the cross-sectional are of the stenopaeic opening in the anterior surface of the lens. The dimension "d" is that dimension which permits focusing of an image onto the fovea centralis recognizing that a too large of an aperture will result in a blurred image and a too small aperture will result in a darkened image. The optimum dimension "d" would appear to have a dimension in the range of about 0.5 mm to about 3.0 mm. The preferred size would be in the order of 0.8 mm. However, the size of the dimension and the like would depend upon the factors described hereinbefore in order to select an opening having the appropriate "d" as required for the specific physical dimensions of the eye into which the optical lens is to be implanted.

FIG. 10 illustrates an alternative embodiment wherein the lens body has a single stenopaeic opening 132 located in the center of the lens body 130 and six intraocular stenopaeic holes spaced radially equally therearound at angles of 60°.

FIG. 11 illustrates another embodiment of an optical lens having a lens body 140 having a central stenopaeic opening 142 and ten stenopaeic openings formed therearound and positioned at 36° relative to the stenopaeic opening 142.

FIG. 12 is an illustration of an implantation for an optical lens 80 having stenopaeic openings 82 and 84 implanted in the anterior chamber of an eye. SPecifically, tbe resilient support members 88 are located forward of the iris 160 of the eye. Behind the optical lens 80 is the hyaloid membrane 166, known as the posterior capsule, which maintains the vitreous humor 168 within the eye The iris 160 and the ciliary processes 164 define the iridiocapsular cleft 162 which is located in the posterior chamber of the eye.

FIGS. 13 and 14 illustrate the implantation of optical lens 80, utilizing the teachings of this invention, in the posterior chamber of the eye in two positions.

In FIG. 13, the resilient support means 88 and their associated annular shaped guidance support elements are located in the iridiocapsular cleft 162 which is located between the iris 160 and the ciliary process 164 The hyaloid membrane 166 has an end 170 which is attached the ciliary processes 164. In FIG. 13, the optical lens 88 is positioned forward of the posterior capsule such that the lens part thereof is centered within the pupil. The iris 160 and the ciliary processes 164 support the support elements 88 at one end of the resilient support means therebetween. The hyaloid membrane 166 extends behind the optical lens 88.

In FIG. 14, the optical lens 88 is positioned adjacent the posterior capsule or hyaloid membrane 166 and behind the ciliary processes 164 resulting In the Iens 88 beIn supported by the ciliary processes 164 and hyaloid membrane 166.

FIG. 15 illustrates the use of an optical lens 210 using the teachings of this invention which has been implanted into the cornea 182 in a corneal inlay. Alternatively, the optical lens 200 can be placed over the cornea 182 in a position shown by dashed lens 200 having the at least ona stenopaeic opening 202 and a plurality of spaced stenopaeic openings 204 formed therearound. The dash lens 200 could also be a contact lens.

FIG. 16 is a pictorial representation of a concavo convex lens, shown generally as 214, utilizing the teachings of this invention The concavo-convex lens 214 includes a concave surface 218 and a spaced convex surface 220 An at least one stenopaeic opening 224 is formed in the central area thereof and a plurality of stenopaeic openings 226 are formed therearound. All of the axis of the stenopaeic openings are substantially parallel to each other.

FIG. 17 illustrates the focusing capability of an optical lens having a transparent lens body having at least one stenopaeic opening formed therethrough. In FIG. 17, a biconvex body 300 has an anterior surface 306 and a posterior surface 308. The lens body 308 has the at least one stenopaeic opening 302 formed therethrough and the opening 302 is substantially perpendicular to the top and posterior surface. The opening has a dimension "d" which is selected to be a geometrical dimension which can be described in the following manner. An ob]ect, shown generally as 310, is located outside of the lens implanted in the eye. Light rays are passed from the image 310 and travel toward the lens within a path defined by lines 312. The central axis of the at least one stenopaeic opening 302 is shown by dashed lines 314. Light rays which are essentially parallel to the axis of the stenopaeic opening 302 are passed by the lens along a predetermined light transmitting path defining the visual axis of the eye. The light beams are then focused onto the fovea centralis where an image is formed as shown by arrow 320. The fovea centralis is located in the macula of the eye, which, in turn, is located on the retina of the eye.

Fig. 18 shows in greater detail how the lens selectively intercepts and passes light beams along the predetermined light transmitting path defining the visual axis of the eye. The lens body 300 has an anterior surface 306 and the posterior surface 308. Light rays, shown generally as 322, 334 and 350 impinging upon the lens Light beams 334 and 350 strike the lens surface and are intercepted or rejected by the lens surface Light rays which are substantially parallel to the axis of the stenopaeic opening 302 and which are within the cross-sectional dimension thereof, and these light rays are shown by 322, are passed through the opening 302. The light rays so transmitted pass along the predetermined path defining the visual axis of the eye until they reach the fovea centralis represented as 330. In essence, the lens 300 functions to focus the image on the fovea centralis 330.

However, if the lens cannot focus the image because it is too close or too far, the light passing through the at least one stenopaeic opening passes through the lens and focuses on the fovea centralis. It is well known in the art that the fovea centralis is a small, rodless depression of the retina in line with the visual axis, which affords acute vision.

In this manner, the lens cooperates with the fovea centralis so as to focus the light thereon to obtain an optical effect by increasing the normal depth of focus of the eye, the distance represented as "f" in FIG. 18, to obtain the optical effect by increasing the normal depth of focus of the eye in order to substitute for the loss of at least one of the focusing power and the accommodation of the eye.

It is envisioned that the concept and the teaching of the present invention have wide applications in the field of ophthalmology. For example, it is well known in the art to have contact lens or intraocular lens which have UV filters, colored lens or the like. To the extent that the optical lens are able to pass light rays, sometimes referred to as a translucent lens, the teachings of this invention could have wide application to such optical devices. The term "transparent lens body" is intended to define such lens.

Also, it is envisioned that the advanced state-of-the-art corneal implants, which contained epithelial cells can permit the optical lens to be implanted into the eye by growth of epithelial cells thereacross, can likewise be formed to have an at least one stenopaeic opening formed therethrough.

In addition, improved optical lenses which are adapted to be implanted into either the anterior chamber or posterior chamber of the eye, including optical lenses having ridges or some other type of structure located on the back side of the lens so as to maintain a spacing between the hack of the lens and the posterior capsule can utilize the teachings of this invention.

It is not necessary that the plurality of intraocular stenopaeic holes be any predetermined or a specific number of openings. Also, it is envisioned that each of the openings could have different diameters. For example, a lens body could have at least one stenopaeic opening located at the center thereof having a dimension of 0.8 mm, and the diameter of the holes forming the plurality of stenopaeic openings formed therearound could have diameters which would vary from as small as 0.5 mm to as large as 3.0 mm. When such a lens is implanted into the eye, the brain would focus on the image nearest the optical center of the eye and selectively rejects other images. Also, by varying the sizes of the geometrical dimension of the various stenopaeic openings, a wide range of angular differences between the anatomical center and the optical center of the eye can be accommodated which permits one lens to be utilized for a variety of different patients having different physical eye measurements, characteristics, lens decentration and the like.

Also, it is further envisioned that the stenopaeic openings could have a circular, diamond, rectangular, square, polygon or other geometrical shape with the dimension thereof being selected in accordance with the teachings set forth herein. The preferred shape of the stenopaeic openings is circular shaped, and the dimension "d" would be the diameter thereof.

What is claimed is:

1. An optical lens for an eye for use in a human or animal comprising a clear transparent lens body having a selected diopter power and formed in the central area thereof at least one stenopaeic opening which is located substantially along the central axis of the lens and which is substantially along the central axis of the lens and which is substantially perpendicular to the lens body and having a dimension "d" which is selected to be a geometrical dimension and means for defining a plurality of stenopaeic openings spaced from and positioned around said at least one stenopaeic opening wherein each of said plurality of stenopaeic openings has a selected dimension such that an image of an outside object located on one side of a lens is projected through the lens, through the eye, generally along predetermined light transmitting paths defining the visual axis and lines parallel to the visual axis and onto substantially the same area of the fovea centralis of the eye in a manner to obtain an optical effect by increasing the depth of focus of the eye in order to substitute for the loss of at least one of the focusing power and the accommodation of the eye.

2. The optical lens of claim 1 wherein said at least one stenopaeic opening is circular in shape.

3. The optical lens of claim 1 wherein the dimension "d" is selected to have a geometrical dimension in the range of about 0.5 mm to about 3.0 mm.

4. An optical lens for an eye for use in a human or animal comprising a clear transparent lens body having a selected diopter power, an anterior surface and a posterior surface, said lens body having formed in the central area thereof at least one stenopaeic opening which is located substantially along the central axis of the lens and which is substantially perpendicular to the anterior and posterior surface and having a dimension "d" which is selected to be a geometrical dimension and means for defining a plurality of stenopaeic openings spaced from and positioned around said at least one stenopaeic opening wherein each of said plurality of stenopaeic openings has selected dimension such that an image of an outside object located onone side of hte lens is projected through the lens, through the eye, generally along predetermined light transmitting paths defining the visual axis and liens parallel to the visual axis and onto the fovea centralis of the eye located on the opposite side of the lens to selectively intercept and pass light through the lens body along said visual axis and liens parallel to the visual axis onto substantially the same area of said fovea centralis in a manner to obtain an optical effect by increasing the depth of focus of the eye in order to substitute for the loss of at least one of the focusing power and the accommodation of the eye.

5. The optical lens of claim 4 wherein said at least one stenopaeic opening is circular in shape.

6. The optical lens of claim 4 wherein the dimension "d" is selected to have a geometrical dimension inthe range of about 0.5 mm to about 3.0 mm.

7. The optical lens of claim 5 wherein the lens body is a plano disc lens.

8. The optical lens of claim 4 wherein the lens body is a plano-convex lens.

9. The optical lens of claim 4 wherein the lens body is a bi-convex lens.

10. The optical lens of claim 4 wherein the lens body is a concavo-convex lens.

11. The optical lens of claim 4 wherein the selected dimension of each of said plurality of stenopaeic openings is substantially equal to the dimension "d" of said at least one stenopaeic hole.

12. The optical lens of claim 11 wherein each stenopaeic hole of said plurality of stenopaeic oepnings is spaced equally a distance "s" from the at least one stenopaeic hole.

13. The optical lens of claim 12 wherein the dimension "d" is selected to have a geometric dimension in the range of about 0.5 mm to about 3.0 mm. and the distance "s" is selected to be in the range of about 2.0 mm to about 12 mm.

14. The optical lens of claim 4 wherein said plurality of stenopaeic openings comprises eight stenopaeic openings located at equal angles around said at least one stenopaeic opening.

15. The optical lens of claim 4 wherein all of the stenopaeic openings have a central axis and wherein the central axis of each of the plurality of stenopaeic openings are generally parallel to the central axis of said at least one stenopaeic openings.

16. The optical lens of claim 4 wherein the lens body is a contact lens.

17. The optical lens of claim 4 wherein the lens body is a corneal overlay.

18. The optical lens of claim 4 wherein the lens body is an artificial lens adapted to be implanted into the corneal stroma.

19. The optical lens of claim 4 further comprising
resilient support means operatively coupled to said lens hody and adapted to engage tissue in the chamber of an eye to position the lens in a proper optical relationship to the pupil.

20. The optical lens of claim 19 wherein the optical lens is adapted to be implanted into the anterior chamber of the eye.

21. The optical lens of claim 19 wherein the optical lens is adapted to be implanted into the posterior chamher of the eye.

* * * * *